United States Patent
Bentley et al.

(10) Patent No.: US 10,568,321 B2
(45) Date of Patent: Feb. 25, 2020

(54) QUATERNARY AMMONIUM ACID COMPOUNDS AND COMPOSITIONS FOR DISINFECTION, SANITIZATION, AND CLEANING

(71) Applicant: LONZA INC., Allendale, NJ (US)

(72) Inventors: Marcus Bentley, Brunswick, NJ (US); Andrew Colurciello, Newburgh, NY (US); Danuel Brown, Piscataway, NJ (US)

(73) Assignee: LONZA INC., Allendale, NJ (US)

( * ) Notice: Subject to any disclaimer, the term of this patent is extended or adjusted under 35 U.S.C. 154(b) by 0 days.

(21) Appl. No.: 16/244,640

(22) Filed: Jan. 10, 2019

(65) Prior Publication Data

US 2019/0141998 A1    May 16, 2019

Related U.S. Application Data

(63) Continuation of application No. 14/614,635, filed on Feb. 5, 2015, now abandoned.

(60) Provisional application No. 61/937,090, filed on Feb. 7, 2014.

(51) Int. Cl.
  *A01N 33/12* (2006.01)
  *A01N 59/00* (2006.01)

(52) U.S. Cl.
  CPC ............ *A01N 33/12* (2013.01); *A01N 59/00* (2013.01)

(58) Field of Classification Search
  None
  See application file for complete search history.

(56) References Cited

U.S. PATENT DOCUMENTS

| 6,530,384 B1 | 3/2003 | Meyers et al. |
| 2006/0293202 A1 | 12/2006 | Cate et al. |
| 2007/0141126 A1 | 6/2007 | Hudson et al. |
| 2010/0297207 A1 | 11/2010 | Kemp et al. |

FOREIGN PATENT DOCUMENTS

| EP | 1 001 012 A1 | 5/2000 |
| WO | 2001070030 A2 | 9/2001 |
| WO | 2011/156398 A1 | 12/2011 |
| WO | 2012/090099 A2 | 7/2012 |
| WO | 2012/090101 A2 | 7/2012 |

OTHER PUBLICATIONS

Written Opinion and Search Report of PCT/US2015/014534 dated Apr. 29, 2015.
Weaver et al., "Encyclopedia of Chemical Technology, Disinfectants and Antiseptics", 3rd Ed., vol. 7, pp. 793-832.

*Primary Examiner* — Bethany P Barham
*Assistant Examiner* — Randeep Singh
(74) *Attorney, Agent, or Firm* — McBee Moore & Vanik IP, LLC

(57) ABSTRACT

A disinfecting composition comprising a quaternary ammonium acid compound and hydrogen peroxide is disclosed. An embodiment of the composition comprises a quaternary ammonium acid compound in a hydrogen peroxide/water solution. In addition, the composition can further comprise an acid. In addition, the composition does not comprise a cationic polymer. The disclosure also provides methods of using the same to kill or inhibit the growth of microorganisms, such as bacteria, viruses, fungi, mildew, and mold. The disclosure also provides for methods of disinfecting a substrate, preferably a hard surface, comprising applying a disinfecting composition of the invention to the substrate.

20 Claims, No Drawings

QUATERNARY AMMONIUM ACID COMPOUNDS AND COMPOSITIONS FOR DISINFECTION, SANITIZATION, AND CLEANING

CROSS REFERENCE TO RELATED APPLICATIONS

This application is a Continuation of U.S. patent application Ser. No. 14/614,635, filed Feb. 5, 2015, which is a non-provisional of U.S. Provisional Application No. 61/937,090, filed Feb. 7, 2014. Each of these applications is incorporated by reference in its entirety

BACKGROUND

Field of the Invention

A disinfecting composition comprising a quaternary ammonium acid compound and hydrogen peroxide is disclosed. An embodiment of the composition comprises a quaternary ammonium acid compound in a hydrogen peroxide/water solution. In addition, the composition can further comprise an acid. In addition, the composition does not comprise a cationic polymer. The disclosure also provides methods of using the same to kill or inhibit the growth of microorganisms, such as bacteria, viruses, fungi, mildew, and mold. The disclosure also provides for methods of disinfecting surfaces, preferably a hard surface, comprising applying a disinfecting composition of the invention to the surface.

Pathogenic organisms, such as bacteria, fungi, and viruses, continue to cause infections in humans as well as domestic animals and pets. In recent years, there has been a particular growing concern over food-borne pathogens and the potential for them to contaminate the food chain. Disinfectant formulations have been developed over the last several decades to reduce or destroy pathogenic organisms and accordingly, reduce the rate of infection. Literally any hard surface including floors, walls, countertops, windows, windowsills, sinks, faucets, waste containers, appliances, and cabinet surfaces can become contaminated. Disinfectants have been developed to treat hard surfaces for use in hospitals, rest homes, schools, and homes.

The use of quaternary ammonium compounds (quats) as biocides is well known (See e.g. Kirt-Othmer's Encyclopedia of Chemical technology, $3_{rd}$ Ed., Vol. 7, pp. 793-832, in particular pp. 815-818).

However, quaternium ammonium compounds (i.e., dialkyl quaternary ammonium compound (DDAC) and Dodecyl Dimethyl Benzyl Ammonium Chloride (ADBAC)), while inexpensive and effective biocides, have limitations. For example, when exposed to hard water, efficacy is severely reduced. To compensate, the use of chelants are usually required to sequester water insoluble cations.

The typical quaternium ammonium compound utilizes chloride as the anionic counterion, which when in the presence of metals such as steel, tin, and aluminum can cause corrosion. To compensate, the use of corrosion inhibitors is sometimes necessary.

Proposed quantified standardized method that will be used to evaluate and support antimicrobial activity have shown to demonstrate bias at various level for quat-containing formulas.

Didecyl dimethyl ammonium carbonate/bicarbonate compound (DDABC) does help mitigate (but not totally eliminate) hard water and corrosion issues as described above. However, there are still limiting factors even with this compound. While most chloride-containing quats are stable across much of the pH scale, DDABC is limited to alkaline systems. If attempts are made to utilize the DDABC molecule in neutral or acid systems, the carbonate/bicarbonate reacts, which undesirably releases carbon dioxide gas.

Thus, there is a need for better quaternary ammonium compounds and compositions with improved efficacy against microorganisms.

SUMMARY

In an aspect, the disclosure provides for a disinfecting composition comprising a quaternary ammonium acid compound and hydrogen peroxide with improved anti-microbial efficiency. An embodiment of the composition comprises a quaternary ammonium acid compound in a hydrogen peroxide/water solution. In addition, the composition can further comprise an acid. In addition, the disinfection composition does not comprise a cationic polymer.

In an aspect, the disclosure provides for a quaternary ammonium acid compound with improved anti-microbial efficiency.

In an aspect, the disclosure provides for another disinfecting composition comprising quaternary carbonate/bicarbonate compound, an acid, and hydrogen peroxide with improved efficacy against microorganisms. In an aspect, the composition does not comprise a cationic polymer.

In an aspect, the quaternary ammonium carbonate/bicarbonate compound comprises didecyl dimethyl ammonium carbonate/bicarbonate (DDABC).

In an aspect, the acid comprises one or more of acetic, phosphoric, tartaric, adipic acid, oxalic acid, sulfamic acid, formic acid, citric acid, or glycolic acid.

In an aspect, the disclosure also provides for a method of using the same.

The disclosure also provides for a method of disinfecting surfaces, preferably a hard surface, comprising applying a disinfecting composition of the invention to the surface.

In an aspect, the novel disinfecting composition and novel disinfecting active has improved efficacy against *Pseudomonas aeruginosa* and *Staphylococcus aureus*.

DETAILED DESCRIPTION

In an aspect, the disclosure provides for a disinfecting composition comprising a quaternary ammonium acid compound and hydrogen peroxide with improved anti-microbial efficiency. An embodiment of the composition comprises a quaternary ammonium acid compound in a hydrogen peroxide/water solution. In addition, the composition can further comprise an acid.

The disclosure also provides for a disinfecting composition that does not comprise a cationic polymer. The cationic polymers preferably excluded from the composition may have the following structure:

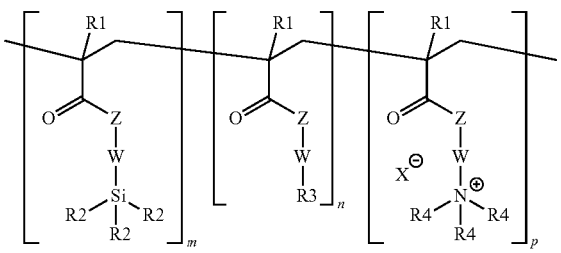

With respect to this structure, R1 may be independently selected from H (hydrogen) or methyl (CH3); R2 may be independently selected from H (hydrogen), halide (fluoride, chloride, bromide, iodide), C1 through C6 alkyl or alkoxy, aryl, linear or branched oligomeric or polymeric dimethyl siloxane; R3 may be independently selected from hydroxyl, alkyl amine, dialkyl amine or polyether; R4 may be independently selected from H (hydrogen), C1 through C6 alkyl, or benzyl; Z may be independently selected from O (oxygen) or NH; W may be independently selected from C1 through C6 alkyl; and X may be independently selected from fluoride, chloride, bromide, iodide, methosulfate or ethosulfate. Alternatively, the monomer represented by subscript "n" may be a vinyl pyrrolidinone. The values of m, n and p may be the same or they may be different. The values of m, n and p are integers and are selected to make the number average molecular weight in the range of 1000 to 100,000 g/mol.

In one aspect, examples of cationic polymers preferably excluded from the composition include cationic polymers that includes a (3-acrylamidopropyl)trimethylammonium chloride monomer combined with another monomer selected from a group consisting of a polar, water-soluble monomer, a hydrophobic, silicone-containing monomer and mixtures of such monomers. The polar, water-soluble monomer may be selected from vinyl pyrrolidinone, hydroxyl ethyl acrylate, hydroxyl ethyl methacrylate, N,N'-dimethyl acrylamide, acrylamide and N-isopropyl acrylamide. The hydrophobic, silicone-containing monomer may be selected from unsubstituted or substituted vinyl or ethynyl group terminated siloxyl compounds, comprising monomethacryloxypropyl terminated polydimethylsiloxane, methacryloxypropyl tris(trimethylsiloxysilane) and methacryloxypropyl terminated T-structure siloxane.

In another aspect, examples of cationic polymers preferably excluded from the composition include cationic polymers that includes a [2-acryloyloxy)ethyl]trimethylammonium chloride monomer combined with another monomer selected from a group consisting of a polar, water-soluble monomer, a hydrophobic, silicone-containing monomer and mixtures of such monomers. The polar, water-soluble monomer may be selected from vinyl pyrrolidinone, hydroxyl ethyl acrylate, hydroxyl ethyl methacrylate, N,N'-dimethyl acrylamide, acrylamide and N-isopropyl acrylamide. The hydrophobic, silicone-containing monomer may be selected from unsubstituted or substituted vinyl or ethynyl group terminated siloxyl compounds, comprising monomethacryloxypropyl terminated polydimethylsiloxane, methacryloxypropyl tris(trimethylsiloxysilane) and methacryloxypropyl terminated T-structure siloxane.

According to WO 2012/090100, the cationic polymers are indicated to provide a durable or persistent activity to kill and prevent the growth of potentially-harmful microorganisms. The cationic polymers of WO 2012/090100 are not present in the compositions of the present invention.

In an aspect, the disclosure provides for a quaternary ammonium acid compound with improved anti-microbial efficiency.

Quaternary ammonium acid compounds useful in the present invention include, but are not limited to, those having the formula (I):

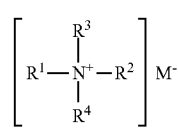

(Formula I)

wherein $R^1$ is a benzyl group or a $C_{1-22}$ alkyl or aryl-substituted alkyl group;

$R^2$ is selected from the group consisting of $C_{1-22}$ alkyl or aryl-substituted alkyl group, benzyl group, and $-[(CH_2)_2-O]_n-R^5$, wherein n is an integer from 1 to 22 and $R^5$ is selected from the group consisting of hydrogen, phenyl, and alkyl-substituted phenyl;

$R^3$ and $R^4$ are independently $C_{1-22}$ alkyl; and $M^-$ is a conjugate base.

In an aspect, $R^1$ and $R^2$ are the same benzyl groups or $C_{1-22}$ alkyl or aryl-substituted alkyl groups.

In an aspect, $R^1$ and $R^2$ are $C_{8-22}$ alkyl. In an aspect, $R^1$ and $R^2$ are $C_{8-12}$ alkyl. In an aspect, $R^1$ and $R^2$ are $C_{10}$ alkyl, preferably n-decyl.

In an aspect, $R^3$ and $R^4$ are the same $C_{1-22}$ alkyl groups. In an aspect, $R^3$ and $R^4$ are $C_1$-$C_4$ alkyl. In an aspect, $R^3$ and $R^4$ are methyl.

In an aspect, M comprises $CH_3COO^-$, $H_2PO_4^-$, $C_4H_5O_6^-$, $C_6H_9O_4^-$, $HC_2O_4^-$, or $H_2NSO_3^-$.

Here and below the expression "$C_{1-22}$ alkyl" is to be understood to comprise all linear or branched alkyl groups having 1 to 22 carbon atoms, including, but not limited to, methyl, ethyl, propyl, isopropyl, butyl, isobutyl, sec-butyl, tert-butyl, pentyl, isopentyl, tert-pentyl, neopentyl, hexyl, heptyl, octyl, nonyl, decyl, dodecyl, tetradecyl, hexadecyl, octadecyl and icosyl. Accordingly, the expression "$C_{8-22}$ alkyl" is to be understood to comprise all linear or branched alkyl groups having 8 to 22 carbon atoms. Accordingly, the expression "$C_{8-12}$ alkyl" is to be understood to comprise all linear or branched alkyl groups having 8 to 12 carbon atoms.

The term "aryl-substituted alkyl group" refers to an alkyl group substituted by one or more aromatic carbon rings, such as ethyl benzyl (the alkyl group being bound to the nitrogen atom). Similarly, the term "aryl-substituted $C_1$-$C_{22}$ alkyl group" refers to a $C_1$-$C_{22}$ alkyl group substituted by one or more aromatic carbon rings.

The expression "alkyl-substituted phenyl" is to be understood to comprise any phenyl group bearing from one to five alkyl groups, in particular $C_{1-22}$ and preferably $C_{1-8}$ alkyl groups as substituents.

In an embodiment, the composition comprises about 0.001 to about 58% by weight (29% active) of one or more quaternary ammonium acid compounds. In a preferred embodiment, the composition comprises about 1 to about 42.5% by weight (21.25% active) of one or more quaternary ammonium acid compounds. In a more preferred embodiment, the composition comprises about 1 to about 6.4% by weight (3.2% active) of one or more quaternary ammonium acid compounds.

In an aspect, the composition may include from about 2% by weight to about 58% by weight of active hydrogen peroxide.

In an aspect, the composition may include from about 1% by weight to about 14% by weight of active acid.

Without being limiting, one of the possible methods to make the disinfecting composition and the quaternary ammonium acid compound comprises reacting a quaternary ammonium carbonate/bicarbonate compound with an acid (either a mineral or organic) prior to hydrogen peroxide addition.

Diagram 1 illustrates a generic reaction reacting quaternary ammonium carbonate/bicarbonate compound with a general acid followed by a hydrogen peroxide addition to yield a quaternary ammonium acid compound. Diagram 2 illustrates a reaction reacting didecyl dimethyl ammonium carbonate/bicarbonate compound with a generic acid followed by a hydrogen peroxide addition to yield a didecyl dimethyl ammonium acid compound. Equation 1 illustrates the result when reacting acetic acid to yield a quaternary ammonium acetate compound.

Diagram 1*:

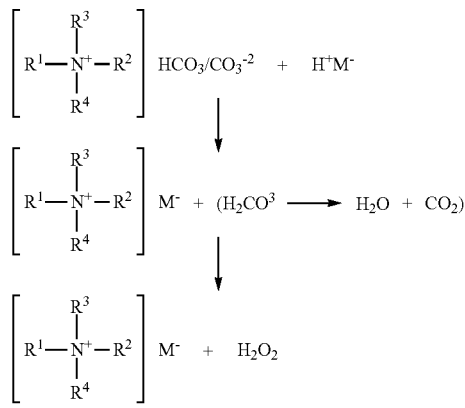

Diagram 2*:

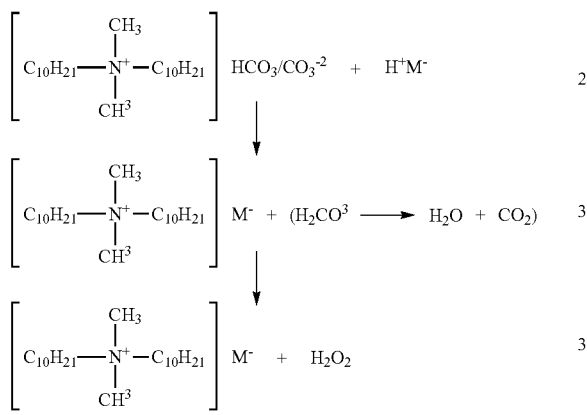

Equation 1:

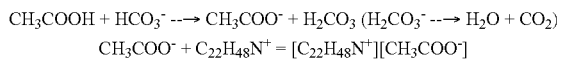

*= (H$^+$M$^-$ represents the generic acid where H$^+$ is the cation and M$^-$ is the anion or conjugate base)

In this method, the disinfection composition and quaternary ammonium acid compound still contains the quaternium ammonium cation, but the bicarbonate/carbonate anion has been replaced with the anion contributed by the reacting acid. It was discovered unexpected that by reacting the quaternary ammonium carbonate/bicarbonate compound with an acid prior to or in presence of hydrogen peroxide, a novel acidified quaternary ammonium compound is created with improved micro efficacy, when compared to quaternary ammonium carbonate/bicarbonate compound alone or previously known quaternary ammonium compounds The disinfecting composition comprising a quaternary ammonium acid compound and hydrogen peroxide is processed by placing the DDABC in a large blending vessel. Water is added to the DDABC and homogenously blended until a clear uniform solution is achieved. The organic or mineral acid is added dropwise (or in small aliquots). The mixture is stirred from 50 to 100 rpm's. The acid reacts with DDABC forming the DDA− conjugate anion salt and releases carbon dioxide. The resultant foam head is contained in the large vessel and goes down slowly as the CO2 is evolved. Concentrated H2O2 (20-35%) is added slowly until a clear solution is achieved.

The disinfecting cleaning composition comprising a quaternary ammonium acid compound, hydrogen peroxide and a surfactant is processed by placing the DDABC in a large blending vessel. Water is added to the DDABC and homogenously blended until a clear uniform solution is achieved. The organic or mineral acid is added dropwise (or in small aliquots). The mixture is stirred from 50 to 100 rpm's. The acid reacts with DDABC forming the DDA− conjugate anion salt and releases carbon dioxide. The resultant foam head is contained in the large vessel and goes down slowly as the CO2 is evolved. Concentrated H2O2 (20-35%) is added slowly until a clear solution is achieved. A peroxide stable surfactant such as Toamine 12-14 from Air Products or FMB-AO8 from Lonza is added and mixed until homogenous.

In an aspect, the disclosure provides for a second composition comprising a quaternary ammonium carbonate/bicarbonate compound, acid, and hydrogen peroxide. In an aspect, the composition does not comprise a cationic polymer. Examples of cationic polymers preferably excluded from the composition are as indicated above.

In an aspect, the quaternary ammonium carbonate/bicarbonate compound has the following formula (II):

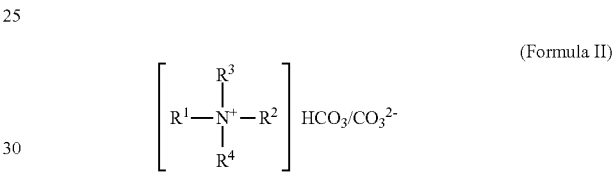

(Formula II)

wherein R$^1$ is a benzyl group or a C$_{1-20}$ alkyl or aryl-substituted alkyl group;

R$^2$ is selected from the group consisting of C$_{1-20}$ alkyl or aryl-substituted alkyl group, benzyl group, and —[(CH$_2$)$_2$—O]$_n$—R$^5$, wherein n is an integer from 1 to 20 and R$^5$ is selected from the group consisting of hydrogen, phenyl, and alkyl-substituted phenyl; and R$^3$ and R$^4$ are independently C$_{1-20}$ alkyl.

In an aspect, R$^1$ and R$^2$ are the same benzyl groups or C$_{1-20}$ alkyl or aryl-substituted alkyl groups.

In an aspect, R$^1$ and R$^2$ are C$_{8-20}$ alkyl. In an aspect, R$^1$ and R$^2$ are C$_{8-12}$ alkyl. In an aspect, R$^1$ and R$^2$ are C$_{10}$ alkyl, preferably n-decyl.

In an aspect, R$^3$ and R$^4$ are the same C$_{1-20}$ alkyl groups. In an aspect, R$^3$ and R$^4$ are C$_1$-C$_4$ alkyl. In an aspect, R$^3$ and R$^4$ are methyl.

In an aspect, the quaternary ammonium carbonate/bicarbonate compound comprises didecyl dimethyl ammonium carbonate/bicarbonate (DDABC).

In an aspect, the acid (H$^+$M$^−$) used in the reaction is any chemical compound that, when dissolved in water, gives a solution with a pH less than 7.0.

In an aspect, the acid is boric, citric, glycolic, sulfuric, nitric, acetic, phosphoric, tartaric, adipic, malic, maliec, oxalic, glutaric, succinic, lactic, fumaric, benzoic, propionic, sorbic, formic, sulfamic, paracetic and/or a combination thereof.

In an aspect, the acid is acetic, phosphoric, sulfamic, or oxalic acid.

The hydrogen peroxide used in the reaction is present to serve as an oxidizer to enhance germ kill.

In an aspect, the composition may include from about 1% by weight to about 58% by weight of the active quaternary ammonium carbonate/biocarbonate compound, based upon 100% total weight of the composition.

In an aspect, the composition may include from about 1% by weight to about 14% by weight of active acid.

In an aspect, the composition may include from about 2% by weight to about 58% by weight of active hydrogen peroxide.

In an aspect, the composition may include about 28% quaternary ammonium carbonate/bicarbonate compound (14% active and all water extracted), about 80% hydrogen peroxide (35% active), and about 6% acid. This can be done if a 35% active solution of hydrogen peroxide is used. This formula, after water is extracted from quaternary ammonium carbonate/bicarbonate compound, adds to 100%.

Hard water tolerance is not a concern in acid media, so the use of chelants is not necessary in the composition of the invention. Therefore, in certain aspects, chelating agents are not present in the composition. Also, since the solution of the invention would not need to contain chloride, the corrosion potential is also dramatically reduced eliminating the need for corrosion inhibitors. See below data:

| Corrosion on Steel* | | |
| --- | --- | --- |
| Active | Total Weight Difference (g) | % Change |
| Dialkyl quaternary ammonium acetate | 0.0032 | 0.000001789 |
| Alkyl dimethyl benzyl ammonium chloride | 0.0105 | 0.05814376 |
| Dialkyl quaternary ammonium chloride | 0.0104 | 0.058350514 |
| Dialkyl quaternary ammonium oxalate | 0.0001 | 0.000567739 |

*= 1000 ppm of active, steel submerged for 24 hours

One acknowledged method for determining micro efficacy is the OECD (Organisation for Economic Co-operation and Development) Quantitative Method for Evaluating Bactericidal Activity of Microbiocides Used on Hard, Non-Porous Surfaces. This method entails inoculating small, stainless steel disks called carriers with inoculum, in the presence of hard water. It is theorized that microorganisms, such as *pseudomonas*, form a biofilm on these carriers. Due to the size of the disk, the presence of a biofilm and the surface tension of the liquid on the disk, this requires qua-based systems to be generally over-formulated to achieve the required efficacy to pass testing. This provides an unfair advantage to both acids and oxidizers used as biocides because of their innate ability to oxidize steel, remove the biofilm without being affected by hard water. This invention combats this issue by combining the biocidal power of quaternary ammonium compound with the oxidizing power of acid.

In an aspect, the disclosure also provides for a method of using the compositions or quaternary ammonium acid compound to kill or to inhibit the growth of microorganisms. In an aspect, the quaternary ammonium acid compound, hydrogen peroxide, and optionally the acid, of the composition are applied together. In an aspect, the quaternary ammonium acid compound, hydrogen peroxide, and optionally the acid, of the composition are applied separately. In an aspect, the quaternary ammonium carbonate/bicarbonate compound, acid, and hydrogen peroxide of the second composition are applied together. In an aspect, the quaternary ammonium carbonate/bicarbonate compound, acid, and hydrogen peroxide of the second composition are applied separately.

In an aspect, the compositions and quaternary ammonium acid compound have improved micro efficacy against a variety of microorganisms that are potentially harmful or capable of causing disease, such as Gram positive and Gram negative bacteria, viruses, fungi, mildew, and mold. Such microorganisms comprise *Staphylococcus*, *Pseudomonas*, hepatitis, rotavirus, rhinovirus, and TB. In an aspect, the compositions and quaternary ammonium acid compound has improved micro efficacy against *S. aureus*, *E. coli*, *Candida albicans*, *Aspergillus niger*, and *P. aeruginosa*, especially *P. aeruginosa* AATC 15442.

The disclosure also provides for a method of disinfecting a surface comprising applying the compositions or quaternary ammonium acid compound to the surface. In an aspect, the quaternary ammonium acid compound, hydrogen peroxide, and optionally the acid, of the composition are applied together. In an aspect, the quaternary ammonium acid compound, hydrogen peroxide, and optionally the acid, of the composition are applied separately. In an aspect, the quaternary ammonium carbonate/bicarbonate compound, acid, and hydrogen peroxide of the second composition are applied together. In an aspect, the quaternary ammonium carbonate/bicarbonate compound, acid, and hydrogen peroxide of the second composition are applied separately.

In one embodiment, the disinfecting compositions further comprise a solvent. In one embodiment, the solvent may be water. In another embodiment, the solvent may be mixtures of ethanol, propylene glycol, isopropanol, or other alcohols and water. In another embodiment, the solvent may be glycol ethers, non-ionic and amphoteric surfactants and chealants.

Optionally, a surfactant may be added as well to the disinfecting compositions. Suitable surfactants include, but are not limited to, amphoteric, surfactants, zwitterionic surfactants, or non-ionic surfactants, for example, amine oxides, linear alcohol ethoxylate, secondary alcohol ethoxylates, ethoxylate esters, betamines, and alkyl polyglycerides. In other embodiments, surfactants are not present.

The compositions of the invention can also include additives, such as chelators, builder salts, dyes, fragrances, nonionic surfactants, wetting agents, and perfluorosurfactants, such as those commonly used in the art of cleaning and disinfecting solutions. The compositions of the invention can also include additives such as a leveling agent, such as those commonly used in the art of coatings or paints. The compositions can also be free of chelants and chloride.

Suitable surfaces include, but are not limited to hard surfaces or food containers. In an aspect, the surface is a hard surface. In a further embodiment, the hard surface is any hard surface found in the home or an industrial or institutional setting. In another embodiment, the hard surface is a floor, wall, countertop, appliance, or fixture.

Surfaces, which may be disinfected with the compositions or quaternary ammonium acid compound, include, but are not limited to, those located in dairies, homes, health care facilities, swimming pools, canneries, food processing plants, restaurants, hospitals, institutions, and industry, including secondary oil recovery. Hard surfaces, such as glass and polished aluminum, are particularly suited for application. Specific areas targeted for application include hard surfaces in the home such as kitchen countertops, cabinets, appliances, waste cans, laundry areas, garbage pails, bathroom fixtures, toilets, water tanks, faucets, mirrors, vanities, tubs, and showers. The compositions can also be used to sanitize floors, walls, furniture, mirrors, toilet fixtures, windows, and wood surfaces, such as fence rails, porch rails, decks, roofing, siding, window frames, and door frames. The compositions, quaternary ammonium acid compound, and disinfecting active are particularly well suited for application on indirect food contact surfaces, such as cutting boards, utensils, containers, dishes, wash basins, appliances, and countertops. The compositions or quaternary ammonium acid compound can be used to sanitize diary plant equipment, milking machines, milk pails, tank trucks, and the like. Areas in hospitals would include beds, gurneys, tables, canisters, toilets, waste cans, stands, cabinets, shower stalls, floors, walls or any other non-porous surface.

The amount of compositions or quaternary ammonium acid compound used to treat a surface is a biocidal effective amount, i.e. that amount to sanitize or disinfect the surface. The biocidal effective amount will depend upon the use intended and can be determined by one of ordinary skill in the art in light of the present detailed disclosure.

Typically, the disinfectant compositions can either be supplied in a dilutable concentrated form or in a ready to use form. A typical concentrate will comprise from about 1% by weight to about 30% by weight of quaternary ammonium acid compounds based upon 100% by weight of total composition and a typical ready to use formulation will comprise from about from 10 ppm to about 10,000 ppm of quaternary ammonium acid compounds based upon total composition.

Treatment of the surface is accomplished by any means known to those of ordinary skill in the art including, but not limited to, dipping, soaking, brushing, spraying, mopping, washing, or the like. The length of treatment required will vary according to treatment conditions, the selection of which is known to those skilled in the art.

One particularly useful application means is to impregnate the disinfecting composition comprising the quaternary ammonium acid compound, hydrogen peroxide, and optionally, an acid, into a wipe substrate. In this embodiment, the wipe is a single use wipe that is impregnated with the disinfecting composition and is stored in a container that will dispense the wipe to a user. The container with the wipes may contain a single wipe, or several wipes. Suitable containers include a pouch containing a single wipe, such as a moist towelette which is torn open by the user, or may be a pouch with a resealable opening containing several wipes in a stacked fashion, a rolled fashion or other suitable formation that would allow a single wipe to be removed from the opening at a time. Pouches are generally prepared form a fluid impervious material, such as a film, a coated paper or foil or other similar fluid impervious materials. In another way to dispense wipes of the present invention is to place the wipe in to a fluid impervious container having an opening to access the wipes in the container. Containers may be molded plastic container with lids that are fluid impervious. Generally, the lid will have an opening to access the wipes in the container. The wipe in the container may be in a interleaved stacked, such that as a wipe is removed from the container the next wipe is positioned in the opening of the container ready for the user to remove the next wipe. Alternatively, the wipe may be a continuous material which is perforated between the individual wipes of the continuous material. The continuous wipe material with perforations may be in a folded form or may be in a rolled form. Generally, in the rolled form, the wipe material is feed from the center of the rolled material. As with the interleaved stack, as a wipe is removed from the container, the next wipe is positioned in the opening for the use to remove the next wipe, when needed.

Disposable wipes provide advantages over other application vehicles, such as a reusable sponge, rag or the like. Unlike sponges, rags and the like, which are used repeatedly, the impregnated wipe is used a single time and disposed of. As is mentioned above, reused sponge or rag presents problems since the sponge or rags may carry microbes that are not easily killed by the disinfecting composition. Further, the disinfecting composition is formulated to treat hard surface, not porous soft surfaces that are present in sponges or rags.

The disinfecting composition can be impregnated into the wipe such that the wipe is pre-moistened and will express or release the disinfecting composition on to the surface as the wipe is run across the surface to be treated. Generally, the disinfecting composition is saturated into the wipe such that the wipe will release the disinfecting composition to the surface through the wiping action. Depending on the wipe substrate, saturation was generally achieved using about 3 wt parts of the use disinfecting composition per 1 wt part of the wipe substrate to be saturated. Generally, the disinfecting composition is used from about 4 part to 6 parts by weight per 1 part by of the wiper substrate. In these ranges, complete saturation of the substrates can be achieved. It is noted that the amount of the disinfecting solution may go up or down to achieve complete saturation of the wipe substrate, depending on the particular wipe substrate.

Suitable wipe substrates include woven and nonwoven materials. Essentially any nonwoven web material may be used. Exemplary nonwoven materials may include, but are not limited to meltblown, coform, spunbond, airlaid, hydroentangled nonwovens, spunlace, bonded carded webs, and laminates thereof. Optionally, the nonwoven may be laminated with a film material as well. The fibers used to prepare the wipe substrate may be cellulosic fiber, thermoplastic fibers and mixtures thereof. The fibers may also be continuous fibers, discontinuous fibers, staple fibers and mixtures thereof. Basis weights of the nonwoven web may vary from about 12 grams per square meter to 200 grams per square meter or more.

In one embodiment the wipe is impregnated with a liquid component containing both active and inert ingredients within the allowable tolerance levels and the disinfecting composition expressed from the wipe contains active ingredients within the allowable tolerance levels. Once applied to the surface, the antimicrobial disinfecting composition is allowed to remain on the surface for a period of time. The antimicrobial composition may be applied to the surface and allowed to dry or may alternatively be dried by wiping the surface with a dry wipe or wiping device, which is preferably unused.

The following examples serve to illustrate certain aspects of the disclosure and are not intended to limit the disclosure.

EXAMPLES

Tables 1 through 4 below represent some of the formulas and laboratory manufacturing process, respectively of the various acids tested. Bardac22c50 is didecyl dimethyl ammonium carbonate/bicarbonate (DDABC).

TABLE 1

| Formulation (Disinfectant Composition) | |
|---|---|
| Ingredient | % By Wt. |
| D.I Water | Q.S. |
| DDABC | 0.5 to 15.0 |
| Acid (100%) | 0.1 to 10.0 |
| Hydrogen Peroxide (30%) | 5.0 to 40.0 |

TABLE 2

Fabrication (Disinfectant Composition)

1: Add DDABC to a large mixing vessel.
2: Add water and blend until a clear uniform solution is achieved.
3: Add acid dropwise under low mixing (50 to 100 RPM's).
4: The resultant foam head will go away as the $CO_2$ is evolved.
5: Add hydrogen peroxide slowly until a clear solution is achieved.

TABLE 3

Formulation (Disinfectant Cleaning Composition)

| Ingredient | % By Wt. |
|---|---|
| D.I Water | Q.S. |
| DDABC | 0.5 to 15.0 |
| Acid (100%) | 0.1 to 10.0 |
| Hydrogen Peroxide (30%) | 5.0 to 40.0 |
| Surfactant (e.g. FMB AO-8 from Lonza) | 0.1 to 20.0 |

TABLE 4

Formulation (Disinfectant Cleaning Composition)

1: Add DDABC to a large mixing vessel.
2: Add water and blend until a clear uniform solution is achieved.
3: Add acid dropwise under low mixing (50 to 100 RPM's).
4: The resultant foam head will go away as the $CO_2$ is evolved.
5: Add hyrogen peroxide slowly until a clear solution is achieved.
6: Add a peroxide stable surfactant like FMB-AO8 from Lonza and mix until homogenous.

Based on microbiological efficacy testing using OECD Quantitative Method for Evaluating Bactericidal Activity of Microbiocides used on Hard, Non-Porous Surface, it was determined that acetic, phosphoric, tartaric, adipic, sulfamic, and oxalic acids provided the greatest level of efficacy. Table 3 summarizes those tests and test conditions.

TABLE 3

OECD[1] results of Quaternium Ammonium Acid Molecule

| Acid | Test 1 | Test 2 |
|---|---|---|
| Tartaric | 4.22 | 3.05 |
| Adipic | 4.21 | 3.52 |
| Boric | 1.13 | — |
| Citric | 3.5 | — |
| Glycolic | 1.99 | — |
| Sulfuric | 3.14 | — |
| Nitric | 1.94 | — |
| Acetic | 5.71 | 4.93 |
| Phosphoric | — | 4.93 |
| Sulfamic | 4.66 | — |
| Oxalic | 5.54 | — |

[1]Test Conditions = 800 ppm Active/375 ppm Hard Water/5% Organic Soil/5 Minute Contact Time Table 3 demonstrates the number of organisms reduced by the different quaternary ammonium acid compounds based on different acids in two different tests. As can be seen above, tartaric acid, adipic acid, acetic acid, phosphoric acid, sulfamic acid, and oxalic acid all resulted in the highest number of organisms reduced.

Quaternary ammonium carbonate and quaternary ammonium chloride are very similar structurally with the only difference being the ionic bond to a carbonate/bicarbonate anion and to a chloride anion, respectively. Due to the nature of the quaternium ammonium chloride's molecular bonding, the chloride ion is not readily removed from the compound. Therefore, when an acid is added to a quaternary ammonium chloride solution, the resultant product is simply chloride quat in an acid media. To determine if adding acid to a chloride quat solution provides any benefit over a neutral or alkaline solution, further OECD micro efficacy tests were conducted. Table 4 summarizes these results.

TABLE 4

OECD[1] Results of Quaternium Ammonium Chloride in Acid Solution

| Acid | $Log_{10}$ Reduction vs. Pa |
|---|---|
| Citric | <2.82 |
| Water | <2.82 |
| Acetic | <2.74 |
| Adipic | <2.74 |
| Tartaric | <2.74 |
| Quat Carbonate* | <2.82 |

[1]Test Conditions = 800 ppm Active/375 ppm Hard Water/5% Organic Soil/5 Minute Contact Time Overall, log reductions of chloride quats in acid solution were significantly lower than quaternary ammonium acid compounds. These tests confirm that the new compound that is being formed is in fact, more efficacious than typically available quats in acid solution, when tested under the same conditions.

In summary, the anti-microbial activity of the instant compositions, quaternary ammonium acid compounds, and disinfecting active demonstrate increased anti-microbial activity than prior quaternary ammonium compounds.

The invention claimed is:

1. A composition comprising a quaternary ammonium acid compound and hydrogen peroxide, wherein the composition does not comprise a cationic polymer,
wherein the quaternary ammonium acid compound is a compound having the formula (I):

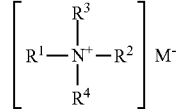

(Formula I)

wherein $R^1$ is a benzyl group or a $C_{1-22}$ alkyl or aryl-substituted alkyl group;
$R^2$ is selected from the group consisting of $C_{1-22}$ alkyl or aryl-substituted alkyl group, benzyl group, and $-[(CH_2)_2-O]_n-R^5$, wherein n is an integer from 1 to 20 and $R^5$ is selected from the group consisting of hydrogen, phenyl, and alkyl-substituted phenyl;
$R^3$ and $R^4$ are independently $C_{1-22}$ alkyl; and
$M^-$ is $CH_3COO^-$, $H_2PO_4^-$, $C_4H_5O_6^-$, $C_6H_9O_4^-$, $HC_2O_4^-$, or $H_2NSO_3^-$,
wherein the quaternary ammonium acid compound is free of chloride, and
wherein the composition has a pH <7.

2. The composition according to claim 1, further comprising an acid.

3. The composition according to claim 1, wherein $R^1$ and $R^2$ are the same benzyl groups or $C_{1-22}$ alkyl or aryl-substituted alkyl groups.

4. The composition according to claim 1, wherein $R^3$ and $R^4$ are the same $C_{1-22}$ alkyl groups.

5. The composition according to claim 1, wherein $R^1$ and $R^2$ are $C_{10}$ alkyl, and $R^3$ and $R^4$ are methyl.

6. A method of killing or inhibiting growth of microorganisms or disinfecting a surface by applying the composition of claim 1 to a surface.

7. The method according to claim 6, wherein the microorganisms comprise one or more of Gram positive bacteria, Gram negative bacteria, viruses, fungi, mildew, or mold.

8. The method according to claim 6, wherein the microorganisms comprise one or more of *Staphylococcus*, *Pseudomonas*, hepatitis, rotavirus, *rhinovirus*, or TB.

9. The method according to claim 6, wherein the microorganisms are *P. aeruginosa*.

10. The method of claim 6, wherein the surface is a floor, wall, countertop, appliance, or fixture.

11. A wipe saturated with a composition of claim 1.

12. The wipe of claim 11, wherein the wipe is disposable, and wherein the wipe expresses or releases the composition on to a surface as the wipe is run across the surface to be treated.

13. The composition of claim 1, comprising about 1% to about 42.5% by weight of quaternary ammonium acid compound and about 2% to about 58% by weight of hydrogen peroxide.

14. The composition of claim 1, comprising about 1% to about 6.4% by weight of quaternary ammonium acid compound.

15. The composition of claim 1, wherein the quaternary ammonium acid compound is formed from reacting a quaternary ammonium carbonate/ bicarbonate compound with an acid prior to the addition of hydrogen peroxide, wherein the quaternary ammonium carbonate/ bicarbonate compound is a compound having the formula (II)

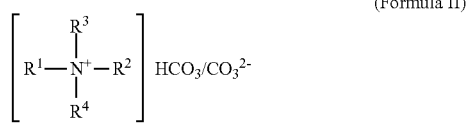

(Formula II)

wherein $R^1$ is a benzyl group or a $C_{1\text{-}20}$ alkyl or aryl-substituted alkyl group;

$R^2$ is selected from the group consisting of $C_{1\text{-}20}$ alkyl or aryl-substituted alkyl group, benzyl group, and $-[(CH_2)_2-O]_n-R^5$, wherein n is an integer from 1 to 20 and $R^5$ is selected from the group consisting of hydrogen, phenyl, and alkyl-substituted phenyl;

$R^3$ and $R^4$ are independently $C_{1\text{-}20}$ alkyl, and wherein the acid is selected from the group consisting of acetic acid, phosphoric acid, tartaric acid, adipic acid, sulfamic acid, or oxalic acid.

16. The composition of claim 15, where the quaternary ammonium carbonate/bicarbonate compound is didecyl dimethyl ammonium carbonate/ bicarbonate.

17. The composition of claim 1, wherein the composition is free of chelating agent.

18. The composition of claim 1, wherein the quaternary ammonium acid compound is a compound having the formula (I):

(Formula I)

wherein $R^1$ is a benzyl group or a $C_{1\text{-}22}$ alkyl or aryl-substituted alkyl group;

$R^2$ is selected from the group consisting of $C_{1\text{-}22}$ alkyl or aryl-substituted alkyl group, benzyl group, and $-[(CH_2)_2-O]_n-R^5$, wherein n is an integer from 1 to 20 and $R^5$ is selected from the group consisting of hydrogen, phenyl, and alkyl-substituted phenyl;

$R^3$ and $R^4$ are independently $C_{1\text{-}22}$ alkyl; and $M^-$ is $CH_3COO^-$, $H_2PO_4^-$, $C_6H_9O_4^-$, $HC_2O_4^-$, or $H_2NSO_3^-$.

19. The composition of claim 1, wherein the composition does not comprise a surfactant.

20. The composition of claim 1, wherein active components in the composition consists of the quaternary ammonium acid compound and hydrogen peroxide.

* * * * *